United States Patent [19]

Nakai et al.

[11] Patent Number: 4,863,963
[45] Date of Patent: Sep. 5, 1989

[54] NOVEL CINNAMOYLAMIDE DERIVATIVES

[75] Inventors: Hisao Nakai; Hiroshi Terashima, both of Takatsuki; Yoshinobu Arai, Osaka, all of Japan

[73] Assignee: Ono Pharmaceutical Co., Ltd., Osaka, Japan

[21] Appl. No.: 191,195

[22] Filed: May 6, 1988

[30] Foreign Application Priority Data

Jun. 8, 1987 [JP] Japan .................. 62-141533

[51] Int. Cl.$^4$ .................................. A61K 31/195
[52] U.S. Cl. .................. 514/563; 562/435; 562/451; 562/455
[58] Field of Search .............. 514/563; 562/451, 455, 562/435

[56] References Cited

U.S. PATENT DOCUMENTS

| 4,026,896 | 5/1977 | Harita et al. | 514/563 |
| 4,151,303 | 4/1979 | Witte et al. | 562/451 |
| 4,486,597 | 12/1984 | Iizuka et al. | 562/455 |
| 4,536,346 | 8/1985 | Shepherd et al. | 562/455 |

FOREIGN PATENT DOCUMENTS

| 173516 | 3/1986 | European Pat. Off. | 514/563 |
| 2164481 | 8/1973 | France | 514/563 |

Primary Examiner—James H. Reamer
Attorney, Agent, or Firm—Stevens, Davis, Miller & Mosher

[57] ABSTRACT

A cinnamoylamide derivative of general formula:

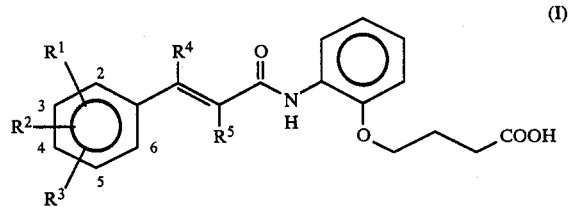

[wherein,
(i) $R^1$, $R^2$ and $R^3$ each represents, same or different, a halogen atom, straight-chain or branched-chain alkoxy group of from 1 to 7 carbon atom(s), straight-chain or branched-chain alkyl group of from 1 to 7 carbon atom(s) or nitro group, and one of $R^4$ and $R^5$ represents a methyl group and the other represents a hydrogen atom, or
(ii) one of $R^1$, $R^2$ and $R^3$ represents a group selected out of
4-isobutyl group,
4-butyl group,
4-propyl group,
4-butoxy group and
4-sec-butyl group, and the other two represent a hydrogen atom,
$R^4$ represents a methyl group and
$R^5$ represents a hydrogen group.]

and non-toxic salts thereof possess an inhibitory activity on 5α-reductase, and therefore is useful for treating and/or preventing agent for alopecia acnes or prostatic hypertrophy.

7 Claims, No Drawings

NOVEL CINNAMOYLAMIDE DERIVATIVES

This invention is related to novel cinnamoylamide derivatives of the following general formula:

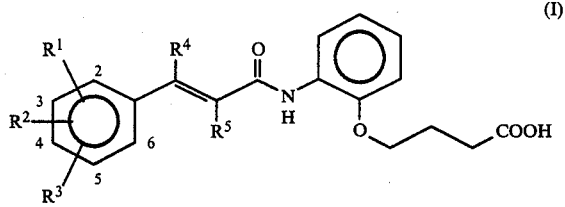

(I)

(wherein all of the symbols are the same measuring as hereafter defined.) and inhihbitory agents on 5α-reductase containing them as active ingredient.

BACKGROUND

So far, many theories are exposited such as (1) imbalance of hormones, (2) genetics, (3) circulatory failure, (4) nutrition, as the origin of androgenic alopecia.

And it has been also suggested that testosterone (androgenic hormone) played an important role on the generation of hairs.

The theory of Adachi at al in which the relation between testosterone and androygenic alopecia is proved by biochemical experiments, is as follows:

(i) first, testosterone biosynthesized in testis is converted into dihydrotestosterone by 5α-reductase existed in hair follicle, sebaceous gland etc. at head.

(ii) dihydrotestosterone reduces the activities of adenyl cyclase remarkably.

(iii) it decreases cyclic-AMP in cells.

(iv) last, it induces lowering of energy generation of hairs and limbus and supressing of protein synthesis (See Biochem. Biophys. Res. Commun., 41, 884 (1970).

According to the theory it is thought that, at the results of the series of the phenomena, hairs in the growing phase shift to the resting phase, the terminal hairs change to the soft hairs, and the androgenic alopecia develops in the end.

A report by H. V. Schweikert supports this theory that large quantities of metabolites by 5α-reductase such as dihydro testosterone etc. in hair follicles of androgenic alopecia patient exist more than that in females or healthy male. (See J. Clin. Endocr., 38. 811 (1974)).

It was reported that dihydrotestosterone converted from testosterone by 5α-reductase also plays in an important physiological role in the generate of acnes (acne, pimple etc.) other than androgenic alopecia. J. B. Hay et al reported that the metabolism of testosterone by 5α-reductase was enhanced in the affected part of acne aggravated, from the study in the flux between affected skin of acne-patient and healthy skin (See Br. J. Dermatol., 91, 123 (1974)).

G. Sansone et al found that synthetic ability of dihydrotestosterone from testosterone developed from two to twenty times in the affected part of acne-patient compared to that in healthy man, and they suggested that dihydrotestosterone generated by 5α-reductase greatly relates to the generation or aggravation of acne (See J. Invest. Dermatol., 56, 366 (1971)).

And, dihydrotestosterone is related to the hypertrophy of prostate. Cowan et al reported that much dihydrotestosterone existed in the prostate of prostatic hypertrophy-patient (See J. Steroid Biochemistry, 11, 609 (1979)). Recently, it was known that activity of 5α-reductase in prostate of prostatic hypertrophy-patient aggravated abnormally (See J. Clinical Endocrinol and Metabolism, 56. 139 (1983)).

From those informations it has been clear that dihydrotestosterone plays an important role in the generation and development of prostatic hypertrophy.

Prior Arts

On the above background, recently, researches and developments of 5α-reductase inhibitors are carried out energetically and they are mainly steroids or derivatives thereof.

Widespread investigation has been carried out in order to discover compounds which have a non-stroidal structure, and possess inhibitory activity on 5α-reductase. The present applicants have found that the above purpose can be accomplished by compounds wherein cinnamic acid or benzoic acids form amides with anilines, and then applied the patents [See Japanese Patent Kokai Nos. 60 97946, 60-116657, 60-142936, 60-142941, 60-146855, 61-126061, i.e. the European Patent Publication No. 173516, Japanese Patent Kokai Nos. 62-198652 and 62-198653.]

For example, in the specification of Japanese Patent Kokai No. 61-126061, it was described that a very wide range of amide compounds possess inhibitory activity on 5α-reductase. Extracting part related closely to the compounds of the present invention of the general formula (I) in chemical structure from it, it is suggested that the compounds of the general formula:

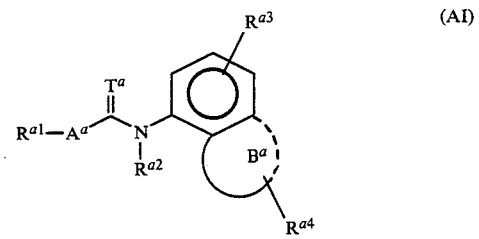

(AI)

[wherein $A^a$ represents a binylene group unsubstituted or substituted by alkyl group(s) of from 1 to 10 carbon atom(s), $B^a$ represents a bibalent group of —O—CH$_2$— and $R^{a1}$ represents a group of the general formula:

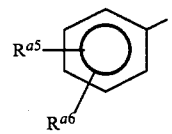

(wherein $R^{a5}$ and $R^{a6}$ represent, independently, a hydrogen atom, halogen atom or alkyl, alkenyl or alkynyl group of from 1 to 20 carbon atom(s) which may be replaced optional carbon atom(s) of from 1 to 5 by an oxygen atom, sulfur atom, halogen atom, nitrogen atom, benzene ring, thiophene ring, naphthalene ring, carbon ring of from 4 to 7 carbon atoms, carbonyl group, carbonyloxy group, hydroxyl group, carboxyl group, azide group or nitro group)
]

$T^a$ represents a oxygen atom, $R^{a2}$ represents a hydrogen atom, $R^{a3}$ represents a hydrogen atom, $R^{a4}$ represents a group of —(CH$_2$) p—COOR$^{a8}$ (wherein ap represents an integer of from 1 to 10, $R^{a8}$ represents a hydrogen atom or an alkyl group of from 1 to 6 carbon atom(s). ]i.e.; the compounds of the general formula:

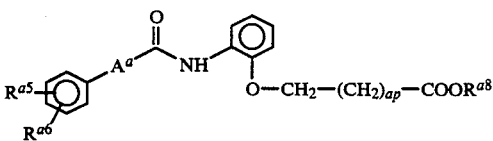 (A2)

(wherein all of the symbols are same meaning as defined hereinbefore.)

On the other hand, the group of compounds which are similar to the compounds of the prevent invention in chemical structure, is disclosed in the specification of Japanese Patent Kokai No. 51-1438 and France Patent Publication No. 2164481.

For example, in the specification of Japanese Patent Kokai No. 51-1438, it is disclosed that the compounds of the general formula

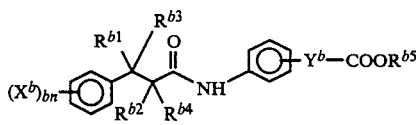 (B)

[wherein $R^{b1}$ and $R^{b2}$ each represent a hydrogen atom or lower alkyl group, $R^{b3}$ represents a chemical bond together with $R^{b4}$.

$X^b$ represents a halogen atom, lower alkyl group, lower alkoxy group or cyclic alkyl group, $b^n$ represents an integer of from 1 to 3, $R^{b5}$ represents a hydrogen atom and $Y^b$ represents an oxyalkylene group binding benzene ring via an oxygen atom. ]

(the above definitions of symbols are extracted from the original specification) is available as antiallergic agent.

Moreover, in the specification of France Patent Publication No. 2164481, it is disclosed that the compounds of the general formula:

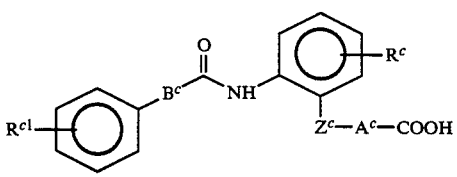 (C)

[wherein $A^c$ represents an alkylene group of from 1 to 3 carbon atom(s), $B^c$ represents a bivalent ethylenic hydro-carbon of from 1 to 5 carbon atom(s), $R^c$ represents a hydrogen atom, $R^{c1}$ represents one or two substituent(s) selected out of an alkyl, cycloalkyl, aryl, aralkyl, halogen, alkoxy, aryloxy and alkylthio group and $Z^c$ represents an oxygen atom.

(the definition of symbols are extracted from the original specification) possess anti-inflammatory and antipyretic action.

[Construction of the invention ]

This time, the present inventors have synthesized the compounds of the general formula (I) which almost belong to the compounds of the general formula (B) broadly and are not described specifically in the specification of European Patent Publication No. 173516, and confirmed that compounds possess inhibitory activity on 5α-reductase. The fact that the compounds of the general formula (B) possess anti-inflammatory activity does not quite suggest that the compounds of the general formula (I) possess inhibitory activity on 5α-reductase.

And, the compounds of the general formula (I) are classified into the compounds included broadly in the general formula (A2) and those excluded from that. It has now been found that the compounds which are not described specifically in the specification of the European Patent Publication No. 173516 possess far more inhibitory activity on 5α-reductase than was expected at the beginning. Applicants have discovered this inhibitory activity by synthesizing the compounds and confirming their activity. It can be quite unexpected that the compounds having remarkably superior activity are contained in the compounds of the general formula (A2). About the latter, we have found that the compounds possess an inhibitory activity on 5α-reductase in spite of remarkable difference in structure.

Examining the specification of France Patent Kokai No. 2164481 in which the compounds of the general formula (C) is disclosed in detail, we can understand that only one compound was synthesized in practice. And, the fact that compounds of the general formula (C) possess anti-inflammatory activity does not quite suggest that the compounds of the present invention possess inhibitory activity on 5α-reductase.

[Disclosure of the invention ]

Accordingly, the present invention is related to cinnamoylamide derivatives of the general formula:

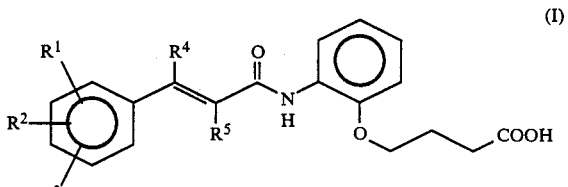 (I)

[wherein, (i) $R^1$, $R^2$ and $R^3$ each represents, same or different, a halogen atom, straight-chain or branched-chain alkoxy group of from 1 to 7 carbon atom(s), straight-chain or branched-chain alkyl group of from 1 to 7 carbon atom(s) or nitro group, and one of $R^4$ and $R^5$ represents a methyl group and the other represents a hydrogen atom, or (ii) one of $R^1$, $R^2$ and $R^3$ represents a group selected out of 4-isobutyl group, 4-butyl group, 4-propyl group, 4-butoxy group and 4-sec-butyl group, and the other two represent a hydrogen atom, R[4] represents a methyl group and
R[5] represents a hydrogen group],
non-toxic salt thereof and inhibitory agents on 5α-reductase containing them as active ingredient.

In the general formula (I), the configuration of a vinylene group which R[4] and R[5] bond to, is E.

When R[1], R[2] and R[3] represents 4-sec-butyl group and the others represent a hydrogen atom, two optical isomers arise owing to an asymmetric carbon atom in the butylgroup. The present invention includes these two isonera and a mixture thereof.

All compounds of the general formula (I) are preferable. Especially, the compounds, wherein,
(i) R[1], R[2] and R[3] each represents, same or different, a group of the general formula:

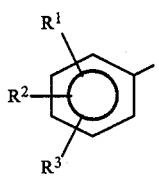

represents a group selected out of
3,5-dichloro-4-pentyloxyphenyl group,
3,5-dimethoxy-4-pentyloxyphenyl group,
3,4,5-tripentyloxyphenyl group,
3,5-dimethyl-4-pentyloxyphenyl gorup,
3,5-di-tert-butyl-4-methoxyphenyl group,
2,3-dichloro-4-pentyloxyphenyl group,
3,5-dichloro-4-butoxyphenyl group,
3,4,5-tripropoxyphenyl group,
3,4,5-tributoxyphenyl group,
2-nitro-4,5-dipentyloxyphenyl group and
3,4,5-triethyoxyphenyl group,
R[4] represents a methyl group and
R[5] represents a hydrogen atom, or
(ii) a group of the general formula:)

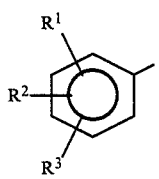

represents
3,4,5-tripentyloxyphenyl group or
3,5-dichloro-4-pentyloxyphenyl group,
R[4] represents a hydrogen atom and
R[5] represents a methyl group, or
(iii) one of R[1], R[2] and R[3] represents a group selected out of
4-isobutyl group,
4-butyl group,
4-propyl group,
4-butoxy group and
4-sec-butyl group, and the other two hydrogen atoms,
R[4] represents a methyl group, and
R[5] represents a hydrogen atom,
are preferable.
More especially, the compounds, wherein,
(i) R[1], R[2] and R[3] each represents, same or different, a group of the general formula :

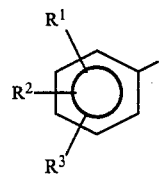

represents
3,5-dichloro-4-pentyloxyphenyl group or
3,5-di-tert-butyl-4-methoxyphenyl group,
R[4] represents a methyl group and
R[5] represents a hydrogen atom, or
a group of the general formula:

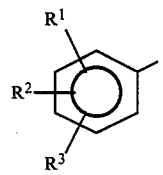

represents
3,4,5-tripentyloxyphenyl group or
3,5-dichloro-4-pentyloxyphenyl gorup,
R[4] represents a hydrogen atom, and
R[5] represents a methyl group,
(ii) one of R[1], R[2] and R[3] represents a group selected out of
4-isobutyl group
4-butyl group,
4-propyl group,
4-butoxy group and
4-sec-butyl group, and
the others represent a hydrogen atom,
R[4] represents a methyl group and
R[5] represents a hydrogen atom,
are preferable.
Most preferable compounds are the compounds, wherein
R[4] represents a methyl group,
R[5] represents a hydrogen atom and
a group of the general formula:

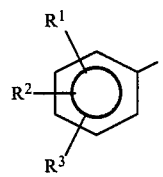

represents a 3,5-dichloro-4-pentyloxyphenyl group or one of R[1], R[2] and R[3] represents a 4-isobutyl group or 4-butyl group.

[Non-toxic salts]

The compounds of the general formula (I), of the present invention may be converted into the corresponding salts by known method. Non-toxic and water soluble salts are preferable. Suitable salts, for example, are follows:
salts of alkaline metal e.g. sodium, potassium,
salts of alkaline earth metal e.g. calcium, magnesium, ammonium salts,
salts of pharmaceutically acceptable amine e.g. tetraalkylammonium salts such as tetramethylammonium, methylamine, dimethylamine, cyclopentylamine, benzylamine, phenethylamine, piperidine, monoethanolamine, diethanolamine, tris (hydroxymethyl)aminomethane, lysine, arginine, N-methyl-D-glucamine.

[Process for the preparation]

According to the present invention, the compounds of the general formula (I) of the present invention may be prepared by spaonifying the compounds of the general formula:

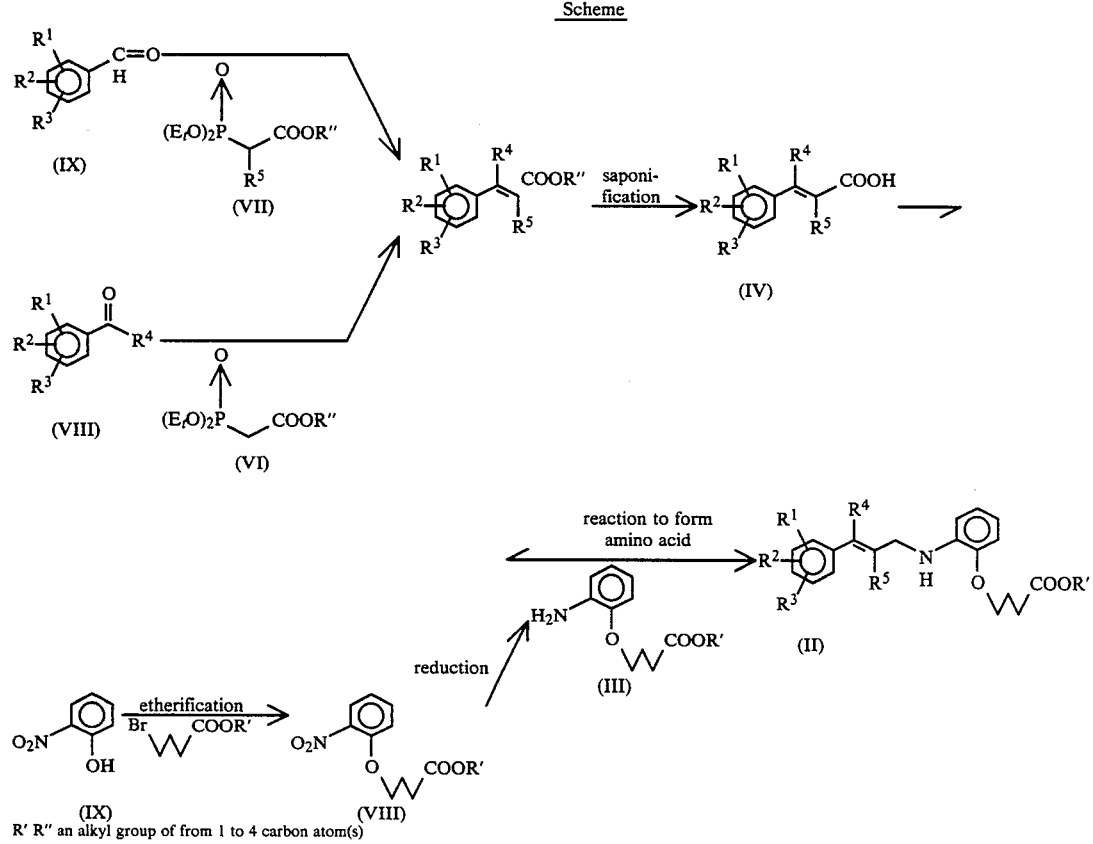

Scheme

R' R" an alkyl group of from 1 to 4 carbon atom(s)

(wherein $R^1$ represents an alkyl group of from 1 to 4 carbon atom(s) and other symbols represent the same meaning as hereinbefore defined.)

The saponification is known and it may be carried out, for example, by using an aqueous solution of alkali (potassium hydroxide, sodium hydroxide, lithium hydroxide potassium carbonate, sodium carbonate etc.) in a water-miscible organic solvent (tetrahydrofuran (THF), dioxane, ethanol, methanol etc.). The reaction is carried out at a temperature of from $-10°$ C. to $100°$ C.

[Process for the Preparation of Intermediates]

The compounds of the general formula (II) may be prepared with using the material compounds of the general formula (VI), (VII), (VIII) and (IX), by the series of reactions shown in the following scheme and the known method.

Throughout the specification, in each reactions, products may be purified by conventional methods, for example, distillation at atmospheric or reduced pressure, high performance liquid chromatography, thin layer chromatography using silica gel or magnesium silicate or washing or recrystallization. Purification may be carried out after each reaction or a series of reactions.

[Starting materials]

Starting materials and reagents in the present invention are known per se or may be prepared by known methods.

For example, a carboxylic acid of the general formula (IV) may be prepared by the method described in the specification of Japanese Patent Kokai Nos. 60-97946, 60-116657, 60-142936, 60-142941 and 60-146855.

An amine of the formula (III) may be prepared by the method described in the specification of Japanese Patent Kokai No. 61-126061.

[Pharmacological Activities of the compounds of the present invention]

The compounds of the general formula (I) of the present invention possess an inhibitory activity on 5α-reductase and therefore are useful for prevention and/or treatment of diseases resulted from the excess generation of dihydrotestosteron in mammals, especially human. The diseases such as above, for example, are alopecia e.g. androgenic alopecia, acnes and hypertrophy of prostate.

An inhibitory activity on 5α-reductase of the present invention is confirmed by the screening system described hereafter.

Inhibitory activity on 5-reductase in vitro (1) The method of test

The test was carried out with reference to the method of J. Shimazaki et al [See Endocrinol, Japon., 18, 179 (1971)).]

Male rat's prostate (4 g) was homogenized with its triple volume of 0.1M HEPES buffer (PH 7.4) including 0.25M cane sugar and was centrifuged at 3000 r.p.m. for 10 mins.

The precipitate was suspended into the buffer solution described above (10 ml), and the suspension was centrifuged at 3000 r.p.m for 5 mins. The resulting precipitate was suspended in the buffer solution(3 ml) described above and was used as a sauce of enzyme.

A reaction mixture (total volume 0.1 ml) of [4-$C^{14}$]-testosterone (1.5 n mol, 1.5×$10^3$ cpm), NADPH (0.5 μmol), enzyme solution (0.03 ml) described above and several kinds of concentration of the compounds in the present invention was incubated for 60 mins at 37° C. Enzyme reaction was quenched by addition of a mixture (0.4 ml) of chloroform and methanol (1:2), and the mixture was centrifuged at 2000 r.p.m for 3 mins. The supernatant (50 μl) was spotted on silica gel thin layer plate. The spot on the plate was developed with a mixture of chloroform, methanol and acetic acid (99.2:0.6:0.2). Radioactivity of dihydrotestosteron generated on plate was measured by TLC scanner of radio-autography and inhibitory ratio was calculated. The result is shown in the following table 1.

TABLE 1

5 α-reductase inhibitory activity (I)

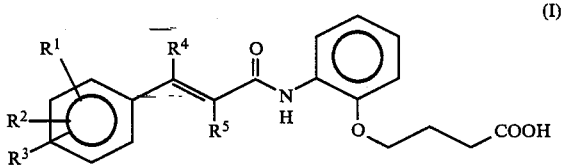

(a) The compounds of the prevent invention containing broadly in the general formula (A2)

| Example No. | $R^1 (R^2 = R^3 = H)$ | $R^4$ | $R^5$ | 5α-reductase inhibitory activity $IC_{50}$ (μM) |
|---|---|---|---|---|
| 1-10 | 4-$CH_2CH(CH_3)_2$ | $CH_3$ | H | 0.11 |
| 1-11 | 4-$(CH_2)_3CH_3$ | $CH_3$ | H | 0.2 |
| 1-12 | 4-$(CH_2)_2CH_3$ | $CH_3$ | H | 0.26 |
| 1-13 | 4-O—$(CH_2)_3CH_3$ | $CH_3$ | H | 0.38 |
| 1-14 | 4-$CH(CH_3)CH_2CH_3$ | $CH_3$ | H | 0.28 |

Compared compound:
Compounds group disclosed specifically in the Specification of the European Patent Publication No. 173516 and have measured inhibitory activity on 5 alpha-reductase practically. 2–5

(b) The compounds of the present invention excluding from the general formula (A2)

| Example No. | $R^1, R^2, R^3$ | $R^4$ | $R^5$ | 5α-reductase inhibitory activity $IC_{50}$ (μM) |
|---|---|---|---|---|
| 1 | 3,5-diCl—4-O$(CH_2)_4CH_3$ | $CH_3$ | H | 0.09 |
| 1-1 | 3,5-di(OCH$_3$)—4-O$(CH_2)_4CH_3$ | $CH_3$ | H | 1.6 |
| 1-2 | 3,4,5-tri[O$(CH_2)_4CH_3$] | $CH_3$ | H | 1.8 |
| 1-3 | 3,5-di$CH_3$—4-O$(CH_2)_4CH_3$ | $CH_3$ | H | 2.1 |
| 1-4 | 3,5-di[C(CH$_3$)$_3$]4-OCH$_3$ | $CH_3$ | H | 1.0 |
| 1-5 | 2,3-diCl—4-O$(CH_2)_4CH_3$ | $CH_3$ | H | 5.6 |
| 1-6 | 3,5-diCl—4-O$(CH_2)_3CH_3$ | $CH_3$ | H | 1.6 |
| 1-7 | 3,4,5-tri[O$(CH_2)_2CH_3$] | $CH_3$ | H | 3.3 |
| 1-8 | 3,4,5-tri[O$(CH_2)_3CH_3$] | $CH_3$ | H | 1.7 |
| 1-9 | 3,4,5-tri[O$C_2H_5$] | $CH_3$ | H | 9.7 |

TABLE 1-continued

5 α-reductase inhibitory activity (I)

| | | | | |
|---|---|---|---|---|
| 1-15 | 2-$NO_2$—4,5-di[O$(CH_2)_4CH_3$] | $CH_3$ | H | 2.2 |
| 1-16 | 3,4,5-tri[O$(CH_2)_4CH_3$] | H | $CH_3$ | 0.53 |
| 1-17 | 3,5-diCl—4-O$(CH_2)_4CH_3$ | H | $CH_3$ | 0.25 |

(2) The result of test

The result of the test shows that all of the compounds of the present invention possess an inhibitory activity on 5α-reductase. A compared compound including in the compounds of the general formula (A2) is the compound which its chemical structure is described specifically and possesses the greatest inhibitory activity on 5α-reductase among the compounds which data on 5α-reductase are concretely in the specification of the invention including the compounds of the present invention broadly (disclosed in European Patent Publication No. 173516 and referred to "the prior invention" hereinafter). It has been confirmed that inhibitory activities on 5α-reductase of the compounds of the present invention are from 5.3 to 18 times as strong as that of the compared compound. It can be quite unexpected that the compounds possessing such a strong activity exist.

And it has been confirmed that the compounds of the present invention which are not included in the compounds of the general formula (A2) and have quite different structures possess a sufficient inhibitory activity.

The compounds of the present invention possess an inhibitory activity on 5-reductase and therefore are useful for prevention and/or treatment of disease resulting from the excess generation of dihydrotestosteron in mammals, especially human. Moreover, it was confirmed that the toxicity of the compounds of the present invention was very low and therefore they may be used as medicine sufficiently safely.

[Application for the Pharmaceuticals]

For the purpose above described, the compounds of the present invention may normally be administered systemically (mainly in the case of prevention and/or treament of prostatic hypertrophy) or partially (mainly in the case of prevention and/or treatment of alopecia and acne), usually by oral or parenteral administration.

The dosage to be administered are determined depending upon age, body weight, symptom, the desired therapeutic effect, the route of administration, and the duration of the treatment etc. In the human adult, for the treatment and/or prevention of prostatic hypertrophy, the dosage per person is generally between 1 mg and 1 g and per dose, by oral administration, up to several times per day, and between 100 μg and 100 mg per dose, by parenteral administration (preferably intravenous administration) up to several times per day.

In the human adult, for the treatment and/or prevention of alopecia and/or acne, the dosage is generally between 10 μg and 50 mg per dose, by dermal administration up to several times per day.

As mentioned above, the dosage to be used depends upon various conditions. Therefore, there are cases in which dosage lower than or greater than the ranges specified above may be used.

In the administration, the compounds of the present invention were administered as solid compositions, liquid compositions and other compositions for oral administration and injections, external compositions and suppositories etc. for parenteral administration.

Solid compositions for oral administration, include compressed tablets, pills, dispersible powders, capsules, and granules. In such compositions, one or more of the active compound(s) is or are, admixed with at least one inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. a lubricating agent (magnesium stearate etc.), disintegrating agents (cellulose calcium gluconate etc.), an assisting agent for dissolving (glutamic acid, aspertic acid etc.), and/or a stabilizing agent (lactose etc.).

The tablets or pills may, if desired, be coated with gastric or enteric material (sugar, gelatin, hydroxypropylcellulose or hydroxypropylmethylcellulose phthalate etc.).

Capsules include soft ones and hard ones.

Liquid compositions for oral administration include pharmaceutically-acceptable emulsions, solutions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agents etc.), sweetening agents, flavoring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.).

For preparation of such spray compositions, for example, the method described in the U.S. Pat. No. 2,868,691 or 3,095,355 may be used.

Injections for parenteral administration include sterile aqueous or non-aqueous solutions, suspensions and emulsions. In such compositions, one or more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be sterilized, for example, by filtration through a bacteria-retaining filter, by incorporation of sterilizing agents in the compositions or by irradiation. They also may be manufactured in the form of sterile solid compositions, for example, by freeze-drying, and which can be dissolved in sterile water or some other sterile diluent for injection immediately before use.

Other compositions for parenteral administration include liquids for external use, and endermic liniments (ointment etc.), suppositories and pessaries which comprise one or more of the active compound(s) and may be prepared by known methods.

Compositions for dermal administration, especially for the treatment and prevention of alopecia and acne, include liquids for external use such as lotion, tonic, spray, solution, suspension, emulsion and liniments such as ointment, gel, cream.

Such compositions may comprise one or more of active ingredient(s) and at least one of inert diluent(s), for example, distilled water, lower alcohols such as ethanol, higher alcohols such as cetanol, poly alcohols such as polyethylene glycol, propylene glycol, celluloses such as hydroxypropyl cellulose, animal or plant fats, vaseline, wax, silicone, plant oil such as olive oil, surfactants, zinc oxide etc.

Besides inert diluents, such composition may also comprise adjuvants (wetting agents, suspending agents, perfuming agents, preserving agents.

[REFERENCE EXAMPLES AND EXAMPLES]

The following reference examples and examples illustrate, but do not limit, the present invention.

The solvents in the parentheses show the developing or eluting solvents and the ratios of the solvents used are by volume in chromatographic separations. Unless otherwise specificed, "IR" were measured by KBr tablet method.

REFERENCE EXAMPLES 1

3-(3,5-dichloro-4-pentyloxyphenyl)-2E-butenoic acid ethyl ester

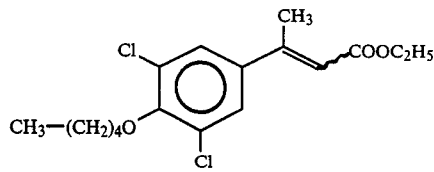

Sodium hydride (content: 63%, 1.53 g) was suspended in tetrahydrofuran (60 ml). A solution of triethyl phosphonoacetate (9.0 g) in tetrahydrofuran (20 ml) was added dropwise to the solution over 30 mins in an ice-bath. A solution of 4-pentylacetophenon (7.4 g) in tetrahydrofuran (20 ml) was added to the solution. The mixture was stirred at 60° C. for 15 hrs and then refluxed for 1 hr. Tetrahydrofuran was removed from the reaction mxiture. The residue was acidified with a diluted hydrochloric acid. The solution was extracted ethyl acetate. The extract was dried over magnesium sulfate and evaporated. The residue was purified by column chromatography on silica gel (n-hexane: ethyl acetate=99:1→98:2→95:5) to give the title compound (E configuration, 9.01 g) having the following physical data:

TLC: Rf 0.68 (benzene).

REFERENCE EXAMPLE 2

3-(3,5-dichloro-4-pentyloxyphenyl)-2E-butenoic acid

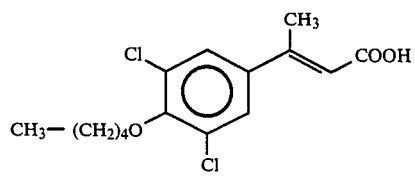

A 4N aqueous solution (26 ml) of sodium hydroxide was added to a solution of ester (prepared in reference example 1, 9 g) in the mixture of methanol (25 ml) and tetrahydrofuran (25 ml). The mixture was stirred for 30 mins at a room temperature and then for 30 mins at 50° C. The reaction mixture was extracted with ether to remove the neutral substance. The water layer was acidified with a 6N hydrochloric acid. The solution was extract with ethyl acetate. The extract was washed with a wawter, dried over magnesium sulfate and evaporated to give crude crystals (8.25 g). The crystals was recrystallized from n-hexane to give the title compound (3.96 g) having the following physical data:

TLC: Rf 0.38 (n-hexane:ethyl acetate =2:1).

REFERENCE EXAMPLE 3

4-(2-nitrophenoxy)butanoic acid ethyl ester

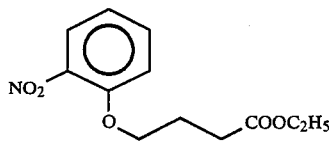

Sodium hydride (content: 62.4%, 16.5 g) was suspended in N,N-dimethylformamide (500 ml). A solution of o-nitropohenol (60 g) in N,N-dimethylformamide (100 ml) was added dropwise to the suspension with stirring in an ice bath over 1 hr. A solution of 4-bromobutanoic acid ethyl ester (84.2 g) in N,N-dimethylformamide (200 ml) was added to the mixture. The mixture was stirred for 15 hrs at about 70° C. N,N-dimethylformamide was removed from the reaction mixture in vacuo. Ethyl acetate (800 ml) was added to the residue. The solution was washed with a water and then saturated brine, dried over magnesium sulfate and evaporated. The residue was purified by column chromatogrpahy on silica gel (n-hexane:ethyl acetate=5:1→3:1) to give the title compound 77.3 g) having the following physical data:

TLC:Rf 0.35 (n-hexane:ethyl acetate=2:1).

REFERENCE EXAMPLE 4

4-(2-aminophenoxy)butanoic acid ethyl ester

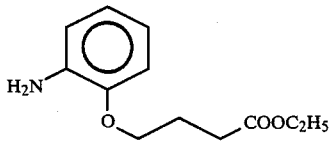

A solution of the nitro compound (prepared in reference example 3, 77.0 g) in ethanol (500 ml) was added to palladium carbon (content: 10 %, 13.1g) suspended in the mixture of chloroform (100 ml) an ethanol (500 ml). The mixture was stirred in an atmosphere of hydrogen for 10 hrs at a room temperature. The reaction mixture was filtered to remove the catalyst. The filtrate was evaporated to give the white solid (79 g).

The obtained solid was dissolved in ethyl actate (1000 ml). A saturated aqueous solution (500 ml) of sodium bicarbonate was added to the solution. The mixture was stirred at a room temperature. The separated oily layer was washed with saturated brine, dried over magnesium sulfate and evaporated. The residue was purified by column chromatography on silica gel (n-hexane:ethyl acetate:methylene chlolride=90:5:5→70:5:15) to give the title compound (60.0 g) having the following physical datea.

TLC: Rf 0.43 (n-hexane:ethyl acetate:methylene chloride=2:1:1)

REFERENCE EXAMPLE 5

4-[2-(3,5-dichloro-4-pentyloxy-β-methylcinnamoylamino)phenoxyl]butanoic acid ethyl ester

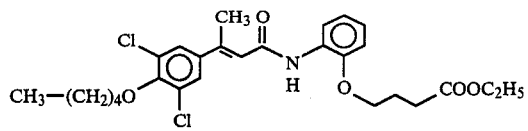

The mixture of butenoic acid (prepared in reference example 2, 3.16 g) and oxalyl chloride (8.7 ml) was stirred for 1 hr at a room temperature. The obtained solution was exaporated to give the coversponding acid chloride.

A solution of acid chloride described above in methylene chloride (10 ml) was added to a solution of an amine (prepared in reference example 4, 2.45 g ) in the mixture of methylene chloride (10 ml) and Pyridine (3 ml) in an ice bath. The mixture was stirred for 1 hr at a room temperature. The reaction mixture was poured into diluted hydrochloric acid. The separated oily layer was washed with a diluted hydrochloric acid, a dilute solution of sodium hydroxide, water, followed by a saturated brine, dried over sodium sulfate and then evaporated to give the title compound (4.5 g) having the following physical data as crude products. The products was used in the following reaction without purification.

TLC: Rf 0.70 (n-hexane:ethyl acetate=2:1).

EXAMPLE 1

4-[2-(3,5-dichloro-4-pentyloxy-β-methylcinnamoylamino) phenoxy]butanoic acid

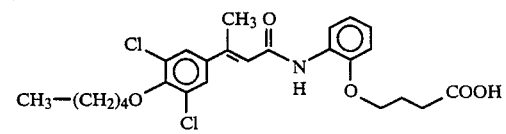

A 2N aqueous solution (7.2 ml) of sodium hydroxide in limited amounts was added to a solution of crude ethyl ester (prepared in reference example 5, 4.5 g) in a mixture of methanol (30 ml) and tetrahydrofuran (15 ml). The mixture was stirred for 30 mins at a room temperature. The reaction mixture was evaporated. A 4N hydrochloric acid (10 ml) was added to the residue. The acidic mixture was extracted with ethyl acetate. The extract was washed with a water followed by a saturated brine, dried over magnesium sulfate, and then evaporated to give crude orystals (3.92 g ). The crystals was recrystallized from a mixture of n-hexane and benzene (2:1) to give the title compound (2.9 g) having the following physical data.

melting point : 122° C.;

TLC: Rf 0.29 (n-hexane:ethyl acetate=2:1);

IR: ν3370, 3100~2300, 1710, 1650, 1620, 1600, 1535, 1450, 1290, 1255, 1220, 1175, 1035, 860, 800, 745 cm$^{-1}$.

Hereinafter, using the corresponding acetophenone instead of 4-pentylacetophenon used in reference example 1, the compounds of the present invention shown in the following Table 2 and Table 3 were obtained by the same procedure as described in reference example 1~5 and example 1.

Moreover, using triethylphosphonopropionate instead of triethylphosphonoacetate, the compounds of the present invention shown in the following table 3 were obtained by the same procedure as described in reference example 1~5 and example 1.

TABLE 2

| Example No. | R¹, R², R³ (structure) | Name | TLC | Melting Point or I R |
|---|---|---|---|---|
| 1-1 | 3,5-dimethoxy-4-pentyloxy substituted phenyl | 4-[2-(3,5-dimethoxy-4-pentyloxy-β-methylcinnomoylamino)phenoxyl] butanoic acid | Rf 0.68 (ethyl acetate) | 96° C. |
| 1-2 | 3,4,5-tripentyloxy substituted phenyl | 4-[2-(3,4,5-tripentyloxy-β-methylcinnamoylamino)phenoxy butanoic acid | Rf 0.38 (n-hexane: ethyl acetate = 2:1) | 85~87° C. |
| 1-3 | 3,5-dimethyl-4-pentyloxy substituted phenyl | 4-[2-(3,5-dimethyl-4-pentyloxy-β-methylcinnamoylamino)phenoxy] butanoic acid | Rf 0.23 (n-hexane: ethyl acetate = 2:1) | 104~106° C. |
| 1-4 | 3,5-di-tert-butyl-4-methoxy substituted phenyl | 4-[2-(3,5-di-tert-butyl-methoxy-β-methylcinnamoylamino)phenoxy] butanoic acid | Rf 0.27 (n-hexane: ethyl acetate = 2:1) | 133~134° C. |
| 1-5 | 2,3-dichloro-4-methoxy substituted phenyl | 4-[2-(2,3-dichloro-4-pentyloxy-β-methylcinnomoylamino)phenoxy] butanoic acid | Rf 0.32 (n-hexane: ethyl acetate = 1:2) | 134~135° C. |
| 1-6 | 3,5-dichloro-4-butoxy substituted phenyl | 4-[2-(3,5-dichloro-4-butoxy-β-methylcinnamoylamino)phenyoxy] butanoic acid | Rf 0.40 (n-hexane: ethyl acetate = 1:1) | ν3320,3200~2000,1725, 1640,1620,1600,1530, 1450,1260,1220,1180, 750 cm⁻¹ |
| 1-7 | 3,4,5-tripropoxy substituted phenyl | 4-[2-(3,4,5-tripropoxy-β-methylcinnamoylamino)phenoxy] butanoic acid | Rf 0.60 (n-hexane: ethyl acetate = 1:1) | ν3375,3300~2200,1730, 1660,1600,1585,1520, 1450,1260,1120 cm⁻¹ (liquid film method) |
| 1-8 | 3,4,5-tributoxy substituted phenyl | 4-[2-(3,4,5-tributoxy-β-methylcinnamoylamino)phenoxyl butanoic acid | Rf 0.27 (n-hexane: ethyl acetate = 2:1) | ν3600~2200,1710,1600, 1580,1530,1450,1260, 1110,760 cm⁻¹ |
| 1-9 | 3,4,5-triethoxy substituted phenyl | 4-[2-(3,4,5-triethoxy-β-methylcinnamoylamino)phenoxy] butanoic acid | Rf 0.25 (n-hexane: ethyl acetate = 1:1) | ν3300,3200~2200,1710, 1650,1615,1580, 1530~1510,1450,1260, 1115 cm⁻¹ |
| 1-10 | 4-isobutyl substituted phenyl | 4-[2-(4-isobutyl-β-methylcinnamoylamino)phenoxy] butanoic acid | Rf 0.08 (n-hexane: ethyl acetate = 3:1) | ν3330,3250~2200,1715, 1640,1600,1530,1450, 1250,1210,750 cm⁻¹ |

TABLE 2-continued

Structure (for examples 1-11 to 1-15):

Cinnamoylamide with R¹, R², R³ on phenyl ring, CH₃ on α-carbon, geometry with amide N-H to phenyl bearing O-(CH₂)₃-COOH ortho substituent.

| Example No. | R¹, R², R³ substituents | Name | TLC | Melting Point or I R |
|---|---|---|---|---|
| 1-11 | 4-butyl | 4-[2-(4-butyl-β-methylcinnomoylamino)phenoxy] butanoic acid | Rf 0.33 (n-hexane: ethyl acetate = 1:2) | 111~112° C. |
| 1-12 | 4-propyl | 4-[2-(4-propyl-β-methylcinnamoylamino)phenoxy] butanoic acid | Rf 0.39 (n-hexane: ethyl acetate = 1:1) | ν3360,3300~2200,1725, 1640,1600,1530,1450, 1180,760 cm⁻¹ |
| 1-13 | 4-butoxy | 4-[2-(4-butoxy-β-methylcinnamoylamino)phenoxy] butanoic acid | Rf 0.44 (n-hexane: = ethyl acetate 1:1) | ν3300,3200~2200,1720, 1650,1610,1530,1450, 1260,750 cm⁻¹ |
| 1-14 | 4-sec-butyl | 4-[2-(4-sec-butyl-β-methylcinnomoylamino)phenoxy] butanoic acid | Rf 0.32 (n-hexane: ethyl acetate = 1:1) | 127.5~129.0° C. |
| 1-15 | 2-nitro-4,5-dipentyloxy | 4-[2-(2-nitro-4,5-dipentyloxy-β-methylcinnomoylamino)phenoxy] butanoic acid | Rf 0.19 (n-hexane: ethyl acetate = 2:1) | 115° C. |

TABLE 3

Structure (for examples 1-16 and 1-17): E-isomer cinnamoylamide with CH₃ on α-carbon.

| Example No. | R¹, R², R³ substituents | Name | TLC | Melting Point or I R |
|---|---|---|---|---|
| 1-16 | 3,4,5-tripentyloxy | 4-[2-(3,4,5-tripentyloxy-β-methylcinnamoylamino)phenoxy] butanoic acid | Rf 0.25 (n-hexane: ethyl acetate = 1:1) | ν3380,1715,1645,1525, 1450,1135,745 cm⁻¹ |
| 1-17 | 3,5-dichloro-4-pentyloxy | 4-[2-(3,5-dichloro-4-pentyloxy-β-methylcinnamoylamino)phenoxy] butanoic acid | Rf 0.15 (n-hexane: ethyl acetate = 1:1) | ν3450,3300~2300,1725, 1660,1615,1600,1540, 1465,1250,760 cm⁻¹ |

PREPARATION EXAMPLE

Preparation of tablets containing 4-[2-(3,5-dichloro-4-pentyloxy-β-methylcinnamoylamino)phenoxy]butanoic acid 4-[2-(3,5-dichloro-4-pentyloxy-β-methylcinnamoylamino)phenoxyl]butanoic acid (5 g), cellulose calcium gluconate (disintegrating agent 200 mg), magnesium stearate (lubricating agent: 100 mg) and microcrystaline cellulose (4.7 g) were admixed in conventional method and punched out to obtain 100 tablets each containing 50 mg of active ingredient.

What is claimed is:

1. A cinnamoylamide derivative of general formula:

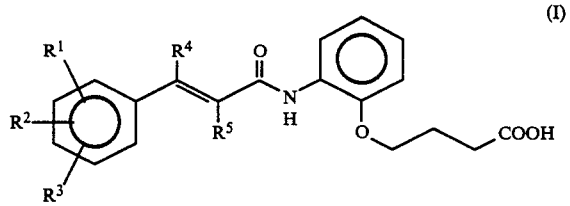

or non-toxic salts thereof.

2. A derivative according to claim 1, wherein
(i) a group of the general formula:

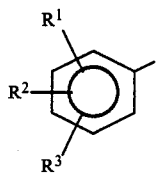

represents a group selected out of
3,5-dichloro-4-pentyloxyphenyl group,
3,5-dimethoxy-4-pentyloxyphenyl group,
3,4,5-tripentylxoyphenyl group,
3,5-dimethyl-4-pentyloxyphenyl group,
3,5-di-tert-butyl-4-methoxyphenyl group,
2,3-dichloro-4-pentylxoyphenyl group,
3,5-dichloro-4-butoxyphenyl group,
3,4,5-tripropoxyphenyl group,
3,4,5-tributoxyphenyl group,
2-nitro-4,5-dipentyloxyphenyl group and
3,4,5-triethoxyphenyl group,
$R^4$ represents a methyl group and
$R^5$ represents a hydrogen atom, or
(ii) a group of the general formula:

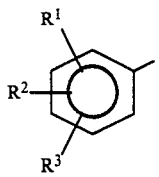

represents
3,4,5-tripentyloxyphenyl group or
3,5-dichloro-4-pentyloxyphenyl group,
$R^4$ represents a hydrogen atom and
$R^5$ represents a methyl group.

3. A derivative according to claim 1, wherein
i) a group of the general formula:

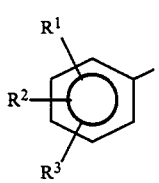

represents
3,5-dichloro-4-pentyloxyphenyl group or
3,5-di-tert-butyl-4-methoxyphenyl group,
$R^4$ represents a methyl group and
$R^5$ represents a hydrogen atom, or
(ii) a group of the general formula:

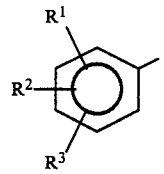

represents
3,4,5-dichloro-4-pentyloxyphenyl group or
3,5-dichloro-4-pentyloxyphenyl group,
$R^4$ represents a hydrogen atom and
$R^5$ represents a methyl group, or
(iii) one of $R^1$, $R^2$ and $R^3$ represents a group selected out of
4-isobutyl group,
4-butyl group,
4-propyl group,
4-butoxyl group and
4-sec-butyl group, and the other two represent a hydrogen atom,
$R^4$ represents a methyl group and
$R^5$ represents a hydrogen atom.

4. A derivative according to claim 3, wherein,
$R^4$ represents a methyl group,
$R^5$ represents a hydrogen atom and a group of the general formula:

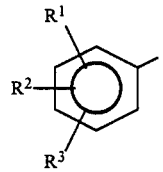

represents 3,5-dichloro-4-pentyloxyphenyl group or one of $R^1$, $R^2$ and $R^3$ represents 4-isobutyl group or 4-butyl group and the other two represent a hydrogen atom.

5. A 5α-reductase inhivitor which comprises a therapeutically effective amount of at least one cinnamoylamide derivative of the formula (I) as defined in claim 1 and a pharmaceutical acceptable carrier and/or coating.

6. A pharmaceutical composition for alleviating disease caused by 5α-reductase for administration containing, as an active ingredient, a therapeutically effective amount of at least one cinnamoylamide derivative of the formula (I) as defined in claim 1 and a pharmaceutical acceptable carrier and/or coating.

7. A method of inhibiting 5α-reductase which comprises administering to mammals, including humans, a therapeutically effective amount of at least one cinnamoylamide derivative of the formula (I) as defined in claim 1.

* * * * *

UNITED STATES PATENT AND TRADEMARK OFFICE
CERTIFICATE OF CORRECTION

PATENT NO. : 4,863,963
DATED : September 5, 1989
INVENTOR(S) : Hisao NAKAI, et al It is certified that error appears in the above-identified patent and that said Letters Patent is hereby corrected as shown below:

In Claim 1, column 19, line 10, (after the formula but before "or non-toxic salts thereof.", please insert:

--[wherein, (i) $R^1$, $R^2$ and $R^3$ each represents, same or different, a halogen atom, straight-chain or branched-chain alkoxy group of from 1 to 7 carbon atom(s), straight-chain or branched-chain alkyl group of from 1 to 7 carbon atom(s) or nitro group, and one of $R^4$ and $R^5$ represents a methyl group and the other represents a hydrogen atom, or

UNITED STATES PATENT AND TRADEMARK OFFICE
CERTIFICATE OF CORRECTION

PATENT NO. : 4,863,963

DATED : September 5, 1989

INVENTOR(S) : Hisao NAKAI, et al

It is certified that error appears in the above-identified patent and that said Letters Patent is hereby corrected as shown below:

(ii) one of $R^1$, $R^2$ and $R^3$ represents a group selected out of 4-isobutyl group, 4-butyl group, 4-propyl group, 4-butoxy group and 4-sec-butyl group, and the other two represent a hydrogen atom, $R^4$ represents a methyl group and $R^5$ represents a hydrogen group.]

Signed and Sealed this

Fifth Day of March, 1991

*Attest:*

HARRY F. MANBECK, JR.

*Attesting Officer*      *Commissioner of Patents and Trademarks*